(12) United States Patent  
Zelickson et al.

(10) Patent No.: US 10,932,765 B1  
(45) Date of Patent: Mar. 2, 2021

(54) FRACTIONATED TISSUE ATTACHMENT DEVICE AND METHOD

(71) Applicant: CUFIX, LLC, Minneapolis, MN (US)

(72) Inventors: Brian Zelickson, Minneapolis, MN (US); Mark Rydell, Minnetonka, MN (US); Al Zelickson, Golden Valley, MN (US)

(73) Assignee: CUFIX, LLC, Minneapolis, MN (US)

( * ) Notice: Subject to any disclaimer, the term of this patent is extended or adjusted under 35 U.S.C. 154(b) by 0 days.

(21) Appl. No.: 16/844,912

(22) Filed: Apr. 9, 2020

Related U.S. Application Data (60) Provisional application No. 62/930,516, filed on Nov. 4, 2019.

(51) Int. Cl.  
*A61B 17/00* (2006.01)  
*A61F 2/00* (2006.01)  
*A61F 2/78* (2006.01)

(52) U.S. Cl.  
CPC ...... *A61B 17/00491* (2013.01); *A61F 2/0059* (2013.01); *A61B 2017/00792* (2013.01); *A61F 2002/7806* (2013.01)

(58) Field of Classification Search  
CPC .... A61B 17/00491; A61B 2017/00792; A45D 44/22; A61F 2/0059  
See application file for complete search history.

(56) References Cited

U.S. PATENT DOCUMENTS

| | | | | |
|---|---|---|---|---|
| 4,854,307 A | * | 8/1989 | Elfenbein | A61B 17/00491 606/204.25 |
| 10,286,161 B2 | * | 5/2019 | Persons | A61M 19/00 |
| 2006/0058892 A1 | * | 3/2006 | Lesh | A61F 2/0059 623/23.72 |
| 2008/0082113 A1 | * | 4/2008 | Bishop | A61B 17/00234 606/151 |
| 2010/0256553 A1 | * | 10/2010 | Fletcher | A61B 17/00491 604/28 |
| 2011/0319944 A1 | * | 12/2011 | Borodic | A61N 1/0502 606/301 |
| 2014/0046362 A1 | * | 2/2014 | Schwartz | A61B 17/0682 606/204.35 |
| 2018/0289467 A1 | * | 10/2018 | Andrade | A61F 2/12 |

* cited by examiner

*Primary Examiner* — Alexander J Orkin  
(74) *Attorney, Agent, or Firm* — Inskeep IP Group, Inc.

(57) ABSTRACT

Methods and devices of tissue attachment with one or more tissue layers being attached using an adhesive to bone or other tissue layers including moving skin and surrounding tissues of the face or any other body part in relationship to the bone or cartilage structures below thus effecting a "skin tightening" or lifting procedure. Methods and devices for minimally invasively locating a precise tissue layer, repositioning the tissue layer in relation to the surrounding tissue layers, creating a specific potential space, delivering an adhesive material within the tissue and depositing an amount of adhesive/sealant material to allow for tissue adhesion.

20 Claims, 9 Drawing Sheets

FRACTIONATED TISSUE ATTACHMENT DEVICE AND METHOD

RELATED APPLICATIONS

This application claims priority to U.S. Provisional Application Ser. No. 62/930,516 filed Nov. 4, 2019 entitled Fractionated Tissue Attachment Device And Method, which is hereby incorporated herein by reference in its entirety.

FIELD OF THE INVENTION

The present invention generally relates to devices and methods of tissue attachment with one or more tissue layers being attached to bone or other tissue layers. More specifically, the present invention relates to moving skin and surrounding tissues of the face or any other body part in relationship to the bone or cartilage structures below thus effecting a "skin tightening" or lifting procedure.

This invention also relates to a device and method which can be used minimally invasively to locate a precise tissue layer, reposition the tissue layer in relation to the surrounding tissue layers, create a specific potential space, transport one or multiple parts of an adhesive/sealant material and preparing the adhesives/sealant, if necessary, during transport within the tissue and depositing the exact amount of adhesive material to allow for tissue adhesion. This is all done with fractionated adhesive points through a small skin incisions (e.g., less than 2 mm) in-situ with biocompatible adhesive materials.

BACKGROUND OF THE INVENTION

The current endoscopic, surgical or open facelift (also known as a rhytidectomy) and brow lift procedures involve the surgical removal of excess skin and tissue from the face and/or brow and the re-draping of the remaining skin of the area. The open facelift procedure involves making a series of bilateral incisions from the temple extending to the preauricular region to the post auricular region to hairline. The open browlift procedure involves incisions extending from temple to temple across the hairline. After the incision is made, the skin and/or underlying tissues are separated from the bone and/or periosteum using blunt dissection, and the skin re-draped and sutured in the new position, with the excess skin being removed.

A variation of the open browlift procedure is the endoscopic browlift in which a series of smaller incisions (10-30 mm) are made at or above the hairline and using blunt dissection and endoscopic guidance the tissue is released from the underlying bone. A variety of techniques such as sutures, screws, bone anchors, bone tunnels and various implants are then used to elevate the tissue and secure the tissue to the underlying bone.

An even more limited approach is the brow-plexy in which similar (15-20 mm) incisions are made below the brow, and wide areas of blunt dissection is again used to separate the soft tissue from underlying bone and various fixation devices and or sutures are used to secure the soft tissue in an elevated position.

All variations of these aesthetic procedures use incisions that are at least 15 mm, require extensive tissue undermining as well as fixation devices that require drilling or perturbation of the bone and or tethering devices such as sutures. Where tissue adhesives have been used it requires a significant tissue dissection and large volume of adhesive material leading to complications such as seroma, hematoma uneven nodules and infection.

There are also many different types of surgical methods for preforming a face lift to improve the appearance of lax aging skin of the face and neck. These methods include subcutaneous, SMAS plication with subcutaneous dissection, minimal access cranial suspension (MACS), extended SMAS, Composite, subperiosteal and modified double plane. (*Arch Plast Surg.* 2015 September; 42(5): 521-531.) (Incorporated by reference) However, the subcutaneous, SMAS and SMAS plication, MACS all require fairly large incisions and due to fixation of tissue located superior to the SMAS have limited durability due to the relaxation of these superficial tissues over a short period of time. The current widely held belief of those in the field is that one needs to perform a widespread dissection deep to the SMAS layer as done in the latter procedures listed above in order to have durable clinical results. (*Arch Plast Surg.* 2015 September; 42(5): 521-531.) (incorporated by reference). These procedures inherently have a greater risk of morbidity with potential nerve and parotid gland injury and longer healing time.

These surgical face lift procedures are also expensive, involve a long and painful recovery period, routinely require general anesthesia and as noted above may be accompanied by complications such as infection, bleeding, nerve damage and complications from anesthesia.

Efforts have been directed lately toward various techniques that involve fixation of skin through the use of permanent or resorbable tacks or anchors to effect facial rejuvenation. However, these procedures still involve the use of significant incisions, requiring a substantial recovery period, and associated surgical, anesthesia, and post-surgical risks.

There is thus a need for less invasive, less expensive methods for reducing the effects of aging and restoring tissue to its natural position on the face and other areas of the body. Such a method also has utility in the treatment of facial paralysis due to stroke, Bell's Palsy, or for facial laxity as a result of trauma.

SUMMARY OF THE INVENTION

The present invention addresses the shortcomings of the prior art as discussed above by providing methods and devices that are minimally invasive, reduce the risk of infection, reduce and improve recovery time, are easily repeatable by users, reduce costs and are applicable beyond dermatology and plastic surgery applications.

According to one aspect, the present invention provides a method for relocating a tissue layer relative to an adjacent bone layer comprising: shifting a tissue layer relative to an adjacent bone layer from an original position to a shifted position without cutting muscle or connective tissue associated with said tissue layer; making multiple small incisions, e.g. 0.5-3 mm, in an outer surface of the tissue layer; using a device which can help reposition the skin and tissue and hold it in place, prepare the deeper layers of tissue to create a space or pocket, e.g., between 1-50 $mm^3$, and of a specific size shape for receiving a precise amount of attachment material and deploying said precise amount of attachment material to prepared area for long term repositioning.

In one embodiment, the device has a proximal end that is used as a handle and has a port with which the attachment material can be inserted, a middle shaft with a channel for attachment material to travers to the distal end, and a distal end that has a dissection portion to precisely prepare the tissue creating a space with specific volume to receive the attachment material, distal member which can grab the tissue to help position the tissue to the correct location in relation to the bone or cartilage and a distal port with which the attachment material can be deposited in the newly created space; wherein such distal end is located, for example, below an epidermis and below a periosteum of the tissue layer.

Another aspect of this invention is the ability to create multiple independent attachment points at any location or pattern, depending upon the clinical indication to provide the optimum directional lift and tension to achieve the best clinical outcome. method contemplates points of attachment that can vary in size, e.g., from 1 mm to 50 mm$^3$ in overall size, and can include one to many points of attachment.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIGS. 3D'-3F' depict alternative steps in the method depicted in FIGS. 3A-3F;

FIGS. 4D'-4F' depict alternative steps in the method depicted in FIGS. 4A-4F;

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements The present invention generally relates to methods and devices for tissue attachment, with one or more tissue layers being attached to bone or other tissue layers. More specifically, the present invention involves repositioning the skin and/or surrounding tissues, of the face or any other body part, in relationship to associated bone, cartilage or tissue structures, then securing the tissue in the new position.

The overall effect is to restore tissue to a preferred position, such as might be done in a browlift or other cosmetic procedure or in orthopedic procedures such as tendon reattachment due to traumatic injuries to the face such as might be caused by automobile accidents or battlefield injuries. The present invention also has utility in treating common tendon avulsion injuries such as mallet or baseball finger. In other words, notwithstanding the specific embodiments disclosed herein in the area of dermatology/plastic surgery, the present invention is useful in many fields beyond those disclosed in the preferred embodiments herein.

As disclosed with respect to specific embodiments below, a method in accordance with the present invention includes moving the soft tissue layer to a new position in relation to the bone or cartilage below; positioning a device through a small incision to the deep layer of bone, cartilage or soft tissue through a superficial soft tissue layer, and repositioning the tissue; holding the superficial soft tissue layer in the new position in relation to the bone, cartilage or soft tissue and creating a precise space or pocket; and, deploying a precise amount of attachment material which will fix the new position of the soft tissue layer without the use of any implantable anchors or sutures. This approach can be used in a plurality of locations allowing for fractional fixation at point adhesions tailored to the specific clinical indication allowing for the optimum tailored clinical result.

Prior to the present invention, the inventors are not aware of any approach to tissue repositioning involving fractionated point fixation without the use of implantable devices or suture material. To date there is no method for durable tissue repositioning of minimal deep dissection through several fractionated point skin incisions using a fixation process which does not require sutures or any other anchoring device that would need to be drilled, screwed or sutured into place. Anyone knowledgeable in the field would tell you this could not be done.

While tissue glue has been used in brow and face lifting procedures, such use has been as merely an adjunct to surgical removal of tissue with large areas of tissue dissection and large incisions and/or the use of implantable devices and/or sutures. For example, there has been at least one known instance of tissue glue in an endoscopic brow lift as a sole attachment material, however, the approach involved a full periosteal forehead dissection and lifting of the whole forehead tissue and removing excess tissue. It did not use or contemplate fractional point fixation in accordance with the present invention. Moreover, an extensive dissection of this nature requires significant healing time and risks of significant side effects such as seroma, bleeding, irregular nodules and infections. It also must be performed under significant patient sedation.

Turning now to specific embodiments depicted in the drawings, FIGS. 1-7 depict a device and method for attaching tissue to bone or cartilage in a shifted position using only small skin incisions less than 2 mm and without requiring drilling or implanting anything into the bone or cartilage. After making an incision through the tissue, which is less than 2 mm, a device of the invention is inserted through this incision to the bone or cartilage and used to prepare the precise space or pocket for the attachment material, which is between 0.1 cc to 5 cc in volume, and then used to reposition the outer tissues. After tissues are located in the correct location, the device is used to deliver the attachment material in the precise amount, being between 0.1 cc to 5 cc in volume, into the prepared space or pocket. The device is then removed, and the tissue held in place with the attachment material.

Figure 1:
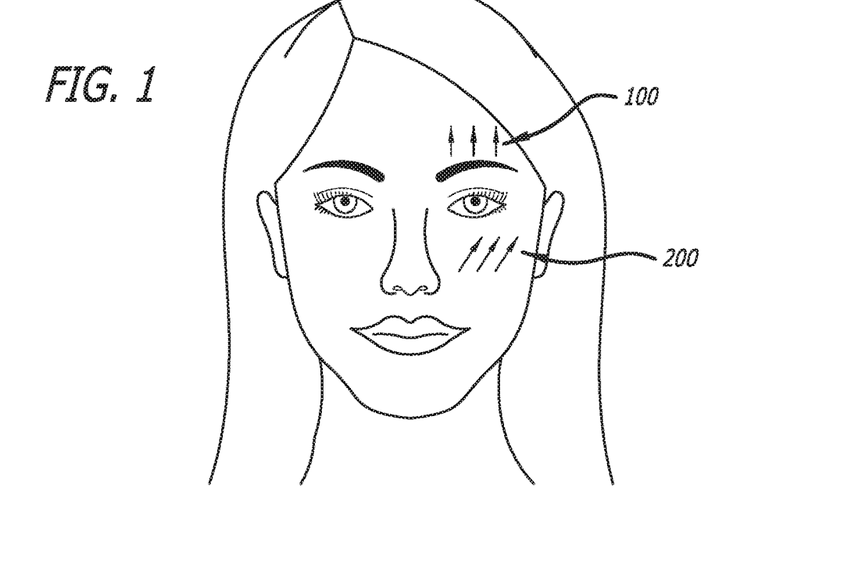
FIG. 1 is a front view of the face of a human depicting example treatment regions in accordance with the present invention.

Referring to FIG. 1, two exemplary treatments on the face of a patient are shown, namely, brow elevation (or brow lift) treatment 100 and facelift treatment 200. The arrows depict the direction in which the treatment will reposition the tissue.

Figure 2A:
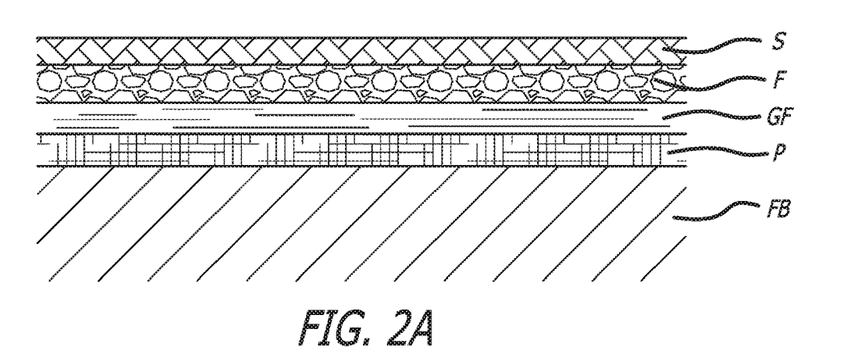
FIG. 2A is a cross-sectional view of facial tissue in the brow area.

Referring to FIG. 2A, the layers of tissue associated with a brow lift treatment 100 include a skin layer S, a fatty layer F, a galea frontalis layer GF, a periosteum layer P and the frontal bone, FB.

Figure 2B:
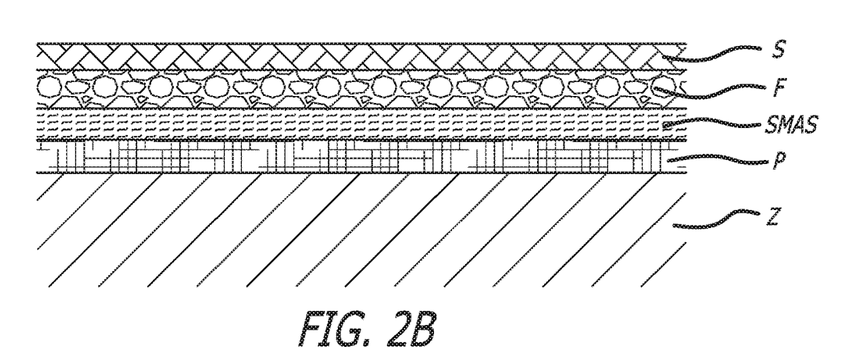
FIG. 2B is a cross-sectional view of facial tissue in the cheek area.

Referring to FIG. 2B, the layers of tissue associated with a facelift treatment 200 include a skin layer S, a fatty layer F, a superficial musculoaponeurotic system layer SMAS, a periosteum layer P, and the zygoma bone Z.

Supra-Periosteal Brow Lift

Figure 3A:
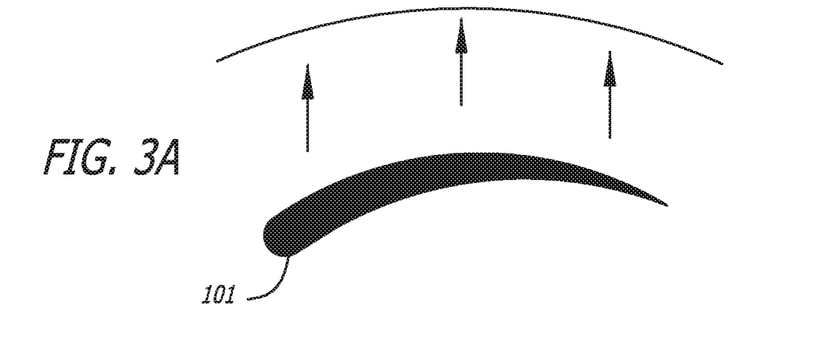
FIGS. 3A-3F depict steps of a method in accordance with one preferred embodiment of the present invention.

Referring to FIG. 3A, the first step in performing a brow lift in accordance with a first embodiment of the invention is to manually displace the tissue associated a patient's brow 101 to the desired position.

Figure 3B:
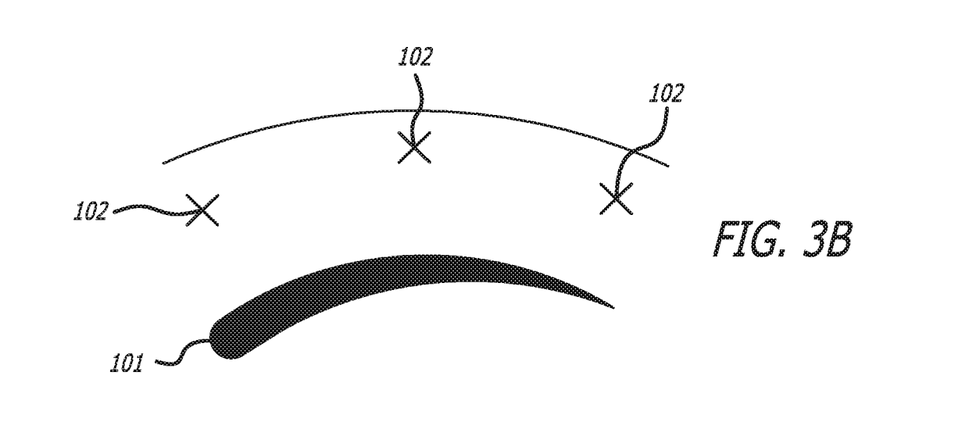

Referring to FIG. 3B, points of fixation 102 (i.e., fixation points) are then determined and, in most cases, marked on the patient signifying where the tissue is to be fixed in order to secure the tissue at the desired position.

Figure 3C:
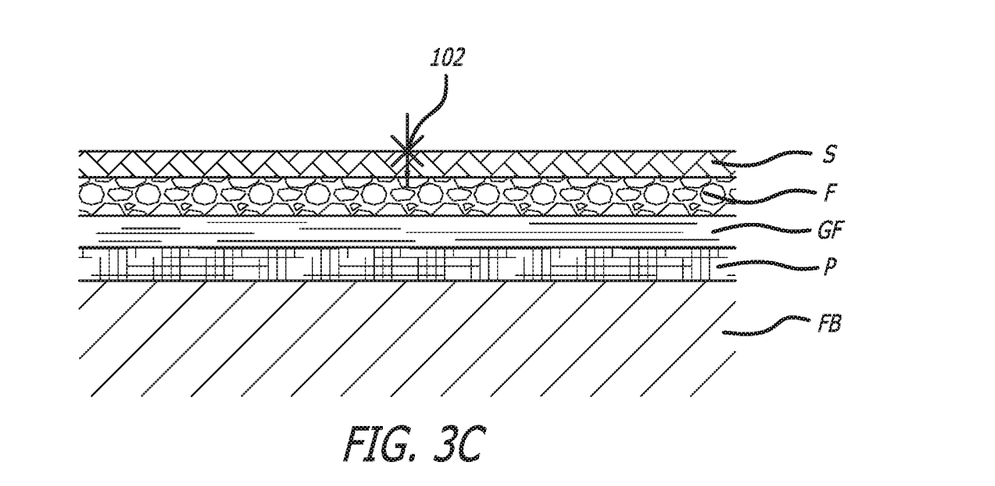
Figure 3D:
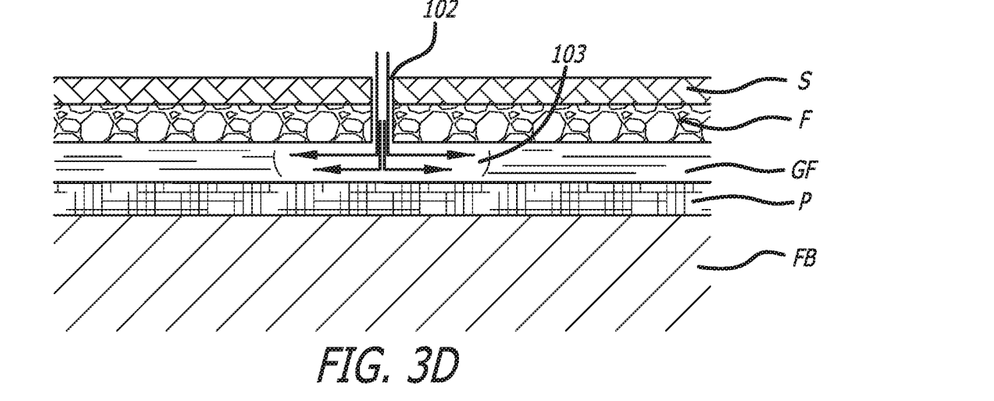

Referring to FIGS. 3C and 3D, a cut is made at each fixation point 102, preferably no more than 2 mm, and a tool used to create a space or pocket 103 in the supra-periosteal plane, i.e. in the plane above the periosteum, i.e., in the GF layer. In a preferred embodiment the pocket 103 is about 2 cm in diameter and has a volume in the range of 0.1 cc to 5 cc.

Figure 3E:
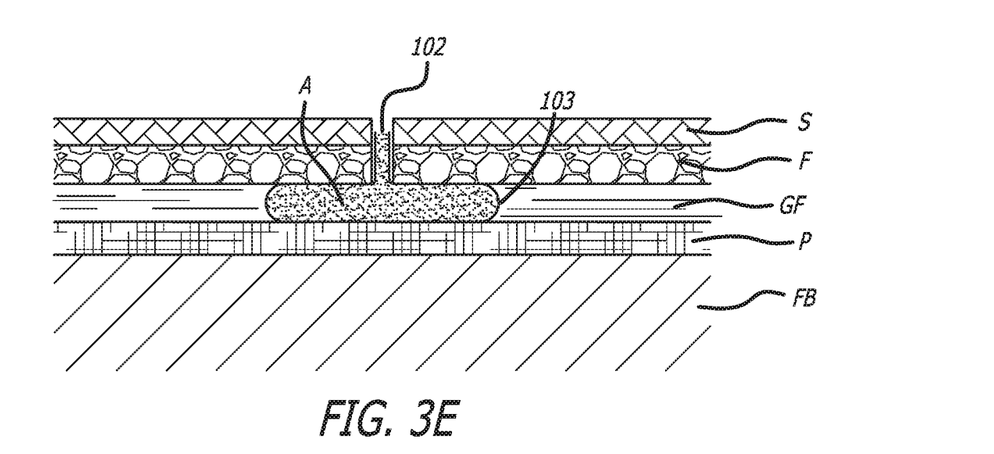
Figure 3F:
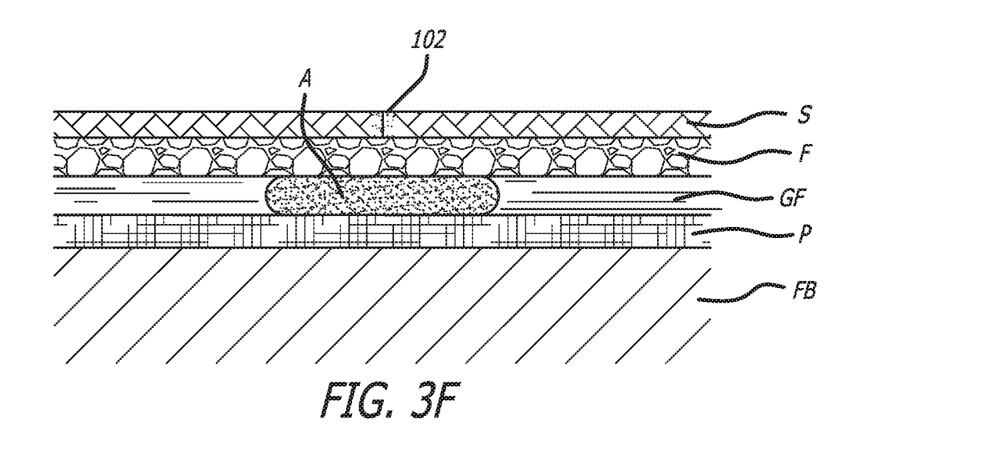

Referring to FIGS. 3E and 3F, an adhesive A is deposited in the pocket 103, the tool removed, the incision closed and the tissue at the fixation point 102 being held in the fixation position until the adhesive A cures and thereby holds the tissue at the new desired position.

These steps are performed for each fixation point 102 needed to secure the brow tissue at the desired position as depicted in FIGS. 3A and 3B.

Subcutaneous Brow Lift

An alternative to the supra-periosteal brow lift treatment is a subcutaneous brow lift treatment, with the primary difference being that the pocket 103 is created in the fatty layer F instead of the GF layer. The first steps of the subcutaneous brow lift treatment are essentially identical to the first steps depicted in FIGS. 3A-3C for the supra-periosteal brow lift treatment. However, as set forth in FIGS. 3A'-3F', the pocket 103 is created in the fatty layer F (FIG. 3D'), the adhesive A then being inserted into the pocket 103 located in the fatty layer F (FIG. 3E') and then the fixation point 102 being held in place until the adhesive A cures and thereby secures the tissue at the new desired position.

These steps are performed for each fixation point 102 needed to secure the brow tissue at the desired position as depicted in FIGS. 3A and 3B.

Supra-Periosteal Facelift

Figure 4A:
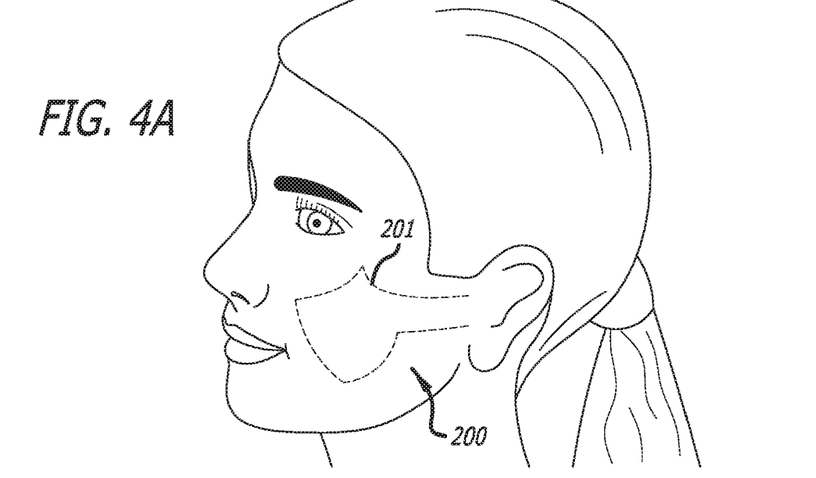
FIGS. 4A-4F depict steps of a method in accordance with one preferred embodiment of the present invention.

Referring to FIG. 4A, the first step in performing a facelift in accordance with a preferred embodiment of the invention is to manually displace the tissue associated a patient's cheek area 201 to the desired position.

Figure 4B:
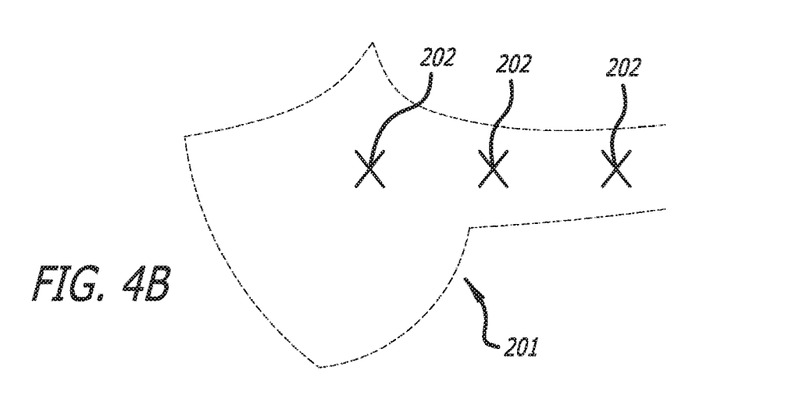

Referring to FIG. 4B, points of fixation 202 (i.e., fixation points) are then determined and, in most cases, marked on the patient signifying where the tissue is to be fixed in order to secure the tissue at the desired position.

Figure 4C:
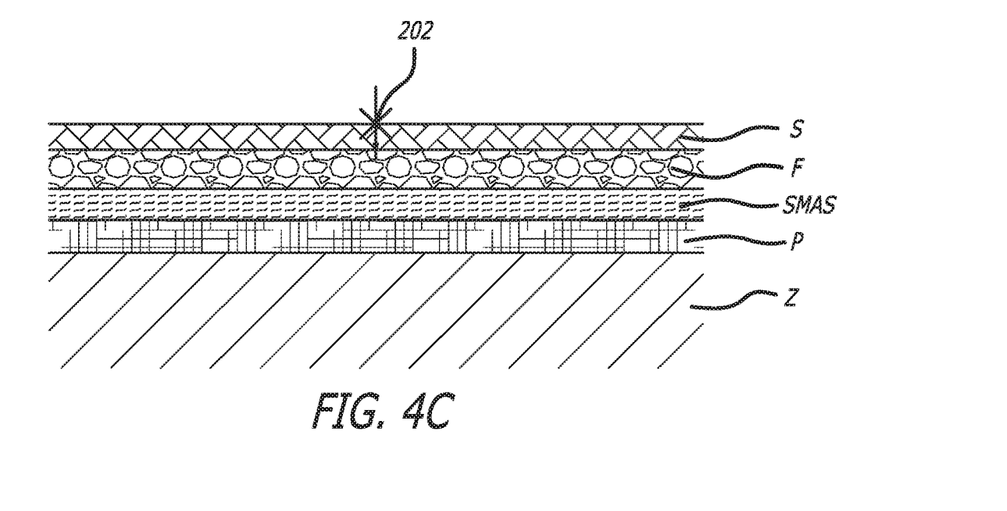
Figure 4D:
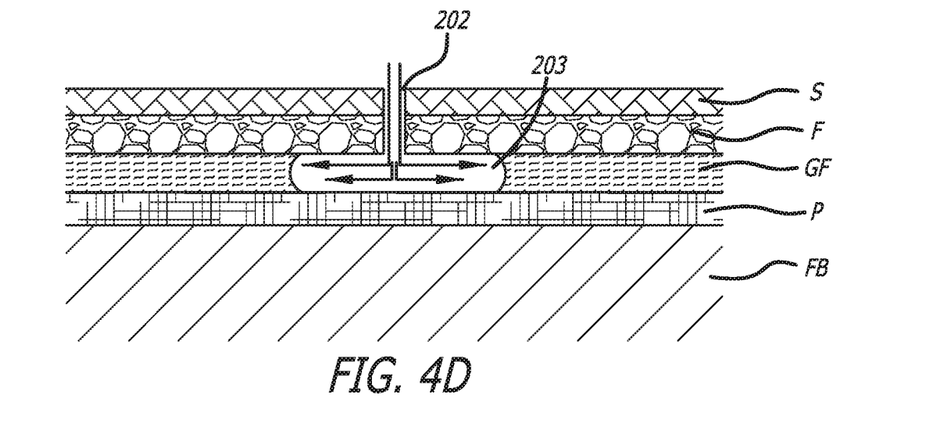

Referring to FIGS. 4C and 4D, a cut is made at each fixation point 202, preferably no more than 2 mm, and a tool used to create a space or pocket 203 in the supra-periosteal plane, i.e. in the plane above the periosteum, i.e., in the SMAS layer. In a preferred embodiment the pocket 203 is about 2 cm in diameter and has a volume in the range of 0.1 cc to 5 cc.

Figure 4E:
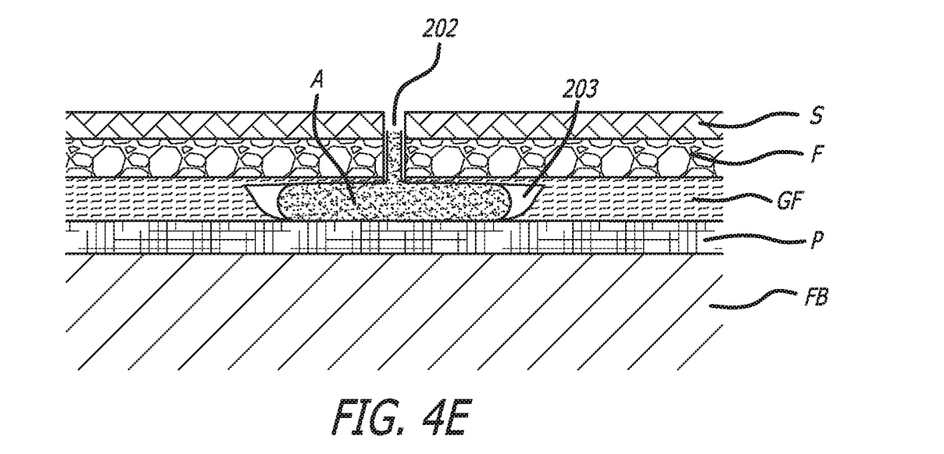
Figure 4F:
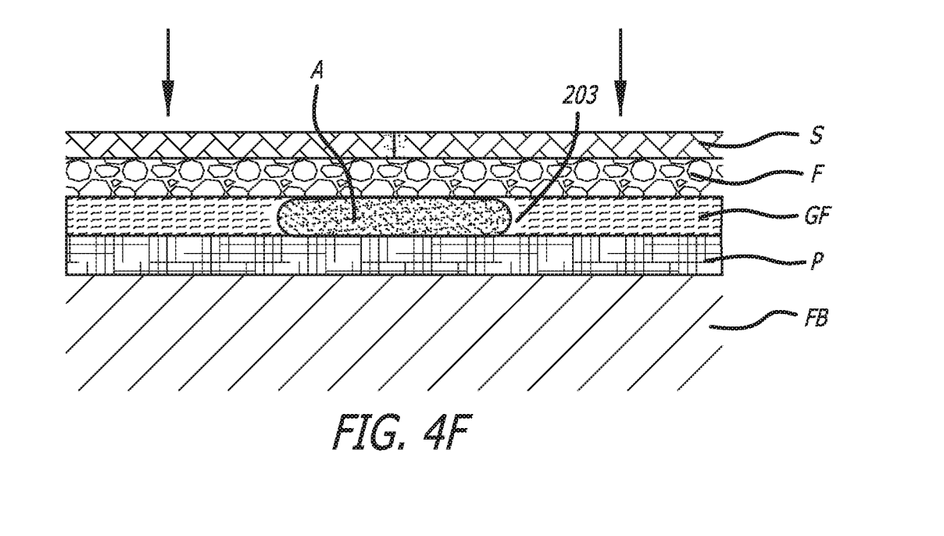

Referring to FIGS. 4E and 4F, an adhesive A is deposited in the pocket 203, the tool removed, the incision closed and the tissue at the fixation point 202 being held in the fixation position until the adhesive A cures and thereby holds the tissue at the new desired position.

These steps are performed for each fixation point 202 needed to secure the brow tissue at the desired position as depicted in FIGS. 4A and 4B.

Subcutaneous Facelift

An alternative to the supra-periosteal facelift treatment is a subcutaneous facelift treatment, with the primary difference being that the pocket 203 is created in the fatty layer F instead of the SMAS layer. The first steps of the subcutaneous brow lift treatment are essentially identical to the first steps depicted in FIGS. 4A-4C for the supra-periosteal facelift treatment. However, as set forth in FIGS. 4D'-4F', the pocket 203 is created in the SMAS layer F (FIG. 4D'), the adhesive A then being inserted into the pocket 203 located in the SMAS layer F (FIG. 4E') and then the fixation point 202 being held in place until the adhesive A cures and thereby secures the tissue at the new desired position.

These steps are performed for each fixation point 202 needed to secure the cheek tissue at the desired position as depicted in FIGS. 4A and 4B.

Figure 5:
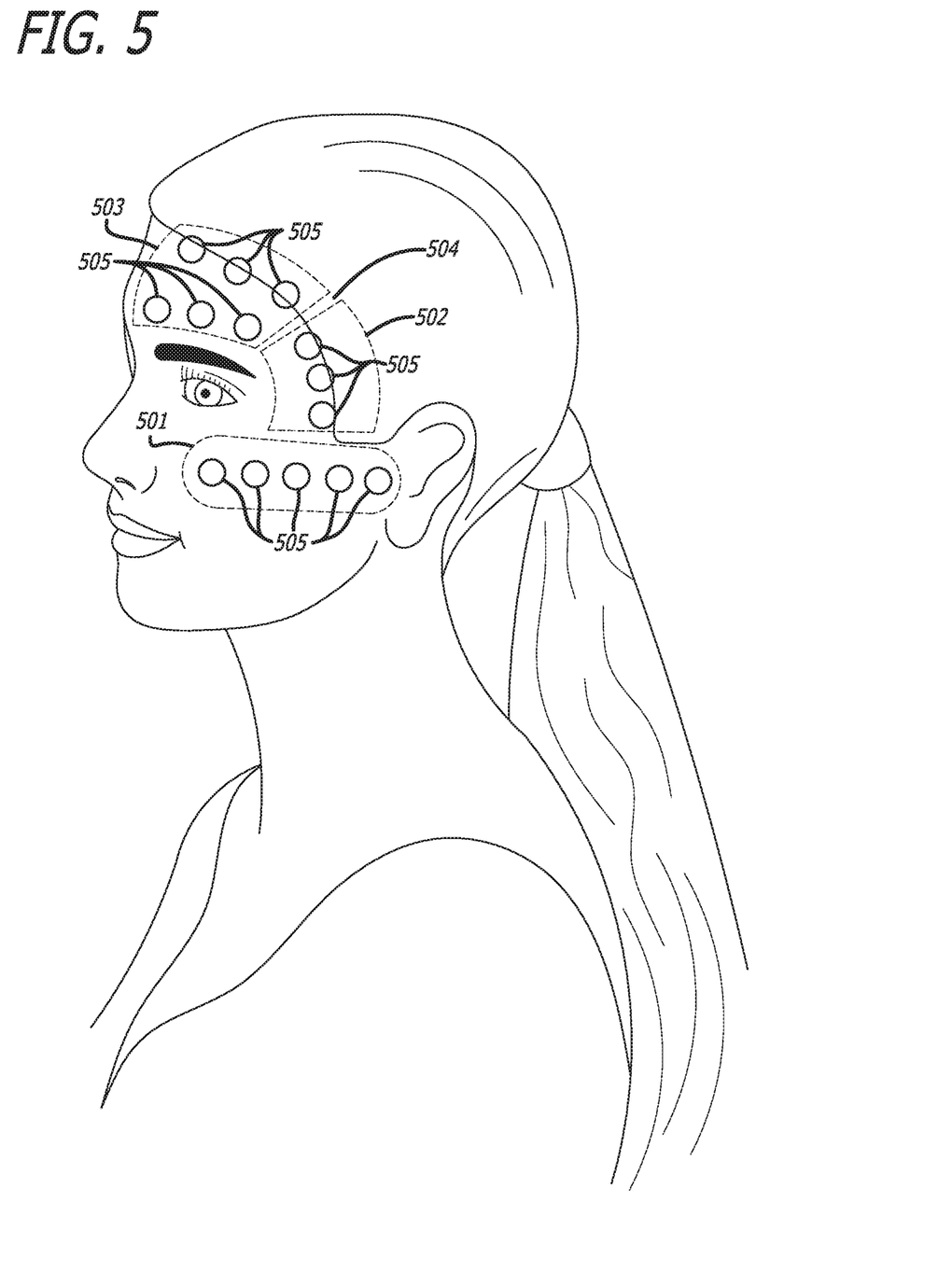
FIG. 5 is a side view of a human face depicting example treatment regions for the present invention.

Referring to FIG. 5, an embodiment of the present invention is depicted on the face of a patient having both a brow lift treatment and a face lift treatment. The round areas 505 are fixation points as discussed above.

In this regard, it is contemplated that in order to achieve optimal treatment results, the dissection level for each fixation point 505 in various regions of the face may be different. For example, the region of the cheek 501, dissection of the fixation points 505 are a subcutaneous dissection, i.e., the pocket is created in the fatty layer F of the tissue.

In the region of the temple 502, the dissection of the fixation points 505 is between superficial and deep fascia.

Lastly, in the region of the brow 503, the dissection of the fixation points 505 are a supra-periosteal dissection, i.e., in the GF layer of the tissue.

Delivery Tool

Figure 6:
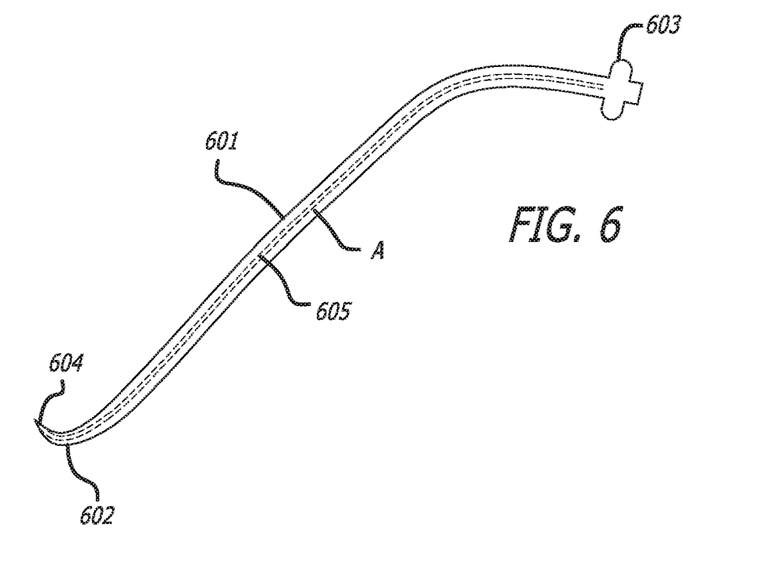
FIG. 6 is an embodiment of a delivery tool in accordance with present invention; and, FIGS. 7A-7C depict steps of a method in accordance with one preferred embodiment of the present invention using the delivery tool of FIG. 6.
Figure 7A:
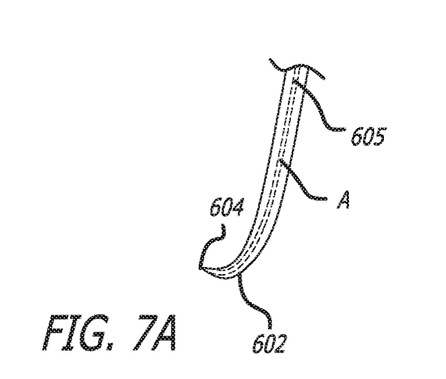
Figure 7B:
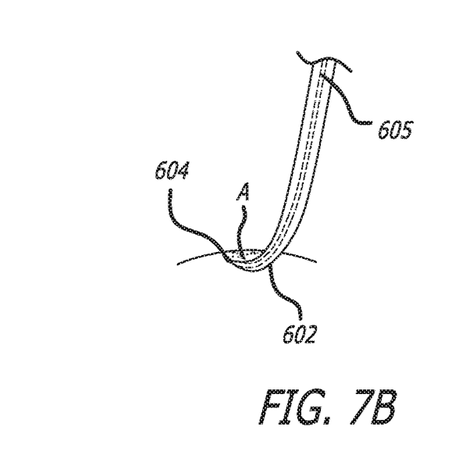
Figure 7C:
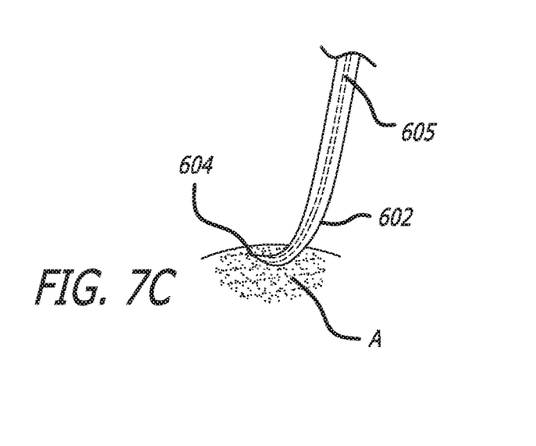

Referring to FIG. 6, a delivery tool 601 is used for creating the pocket space 103, 203 and delivering adhesive A as discussed above. The delivery tool 601 has a proximal end 603 that is used as a handle and has a port with which the adhesive A can be inserted, a middle shaft with a channel 605 for adhesive A to travers to the distal end 602. The distal end has a dissection portion 604 to precisely prepare the pocket space 103, 203 with specific volume to receive the adhesive A. The distal end 602 can grab the tissue to help position the tissue to the correct location in relation to the bone or cartilage. It further includes a distal port with which the adhesive A can be deposited in the pocket space 103, 203 where such distal end 602 is located, for example, below an epidermis and below a periosteum of the tissue layer.

Once a user has made a cut at a fixation point 102, 202, 505, the delivery tool 601 is used to create the pocket space 103, 203 in the desired layer of tissue. A user then urges the adhesive A through the point 604 of the tool 601 to fill the pocket space with adhesive.

In one preferred embodiment, the delivery tool 601 has an internal configuration to mix two or more constituents of a curable adhesive. Representative configurations of such mixing structure can be found in U.S. Pat. No. 6,079,868, the contents of which is incorporated by reference herein.

Adhesive/Sealant

An adhesive/sealant that is biocompatible with human implantation and provides the necessary adhesive strength and durability is preferred for use in the present invention. Examples of such adhesives may include those disclosed in the following U.S. patents, each of which is incorporated herein by reference: U.S. Pat. Nos. 10,391,198; 5,386,606. In one embodiment, the adhesive also promotes healing.

There are many types of biocompatible adhesives/sealants that could be used for this purpose. In preferred embodiments, adhesive/sealants generally fall into 1 of 3 categories.

(1) Natural Polymer-Based Adhesive/Sealants (e.g. Fibrin, Collagen, and Albumin Based)

Examples, include: (a) BioGlue (Cryolife Inc, Kennesaw, Ga.) which is based on Bovine Serum Albumen and glutaraldehyde; (b) PreveLeak (Baxter Healthcare Corporation, Westlake Village, Calif.) which is based on purified BSA and a polyaldehyde.

(2) Synthetic Polymer-Based Adhesive/Sealants (e.g., Polyurethane, Polyethylene Glycol [PEG]

Examples include: (a) Tridyne VS (BD, Franklin Lakes, N.J.) which is based on PEG and human serum albumin; (b) Coseal (Baxter Healthcare Corporation, Westlake Village, Calif.) which is based on 2 cytocompatible PEGs, a dilute hydrogen chloride solution, and a sodium phosphate/sodium carbonate solution.

(3) Polyester-Based and Cyanoacrylate Adhesive/Sealants

Examples include: (a)_Dermabond; (b) Histocryl; (c) Omnex (Ethicon_ which can be absorbable; and, (d) VenaSeal (Medtronic).

Butyl esters provide stronger bond but are rigid. Octyl esters, while providing weaker bond, are more flexible. Blends of octyl cyanoacrylate and n-butyl cyanoacrylate are available (such as GLUture) which offer both flexibility and a strong bond. n-Butyl cyanoacrylate is also used for embolization of cerebral arteriovenous malformations before their surgical treatment. https://en.wikipedia.org/wiki/Butyl_cyanoacrylate, M. Dossi, G. Storti, D. Moscatelli, Synthesis of poly(alkyl cyanoacrylates) as biodegradable polymers for drug delivery applications, in: Macromolecular Symposia 289 (Polymer Reaction Engineering VII), 2010, pp. 124-128 (incorporated herein by reference).

The above is not an exhaustive list as there are other such adhesives/sealants such as citrate-based biomaterials that are seen in nature within mollusks (*Biomater Sci*. 2013 Jan. 1; 1(1): 52-64. doi:10.1039/C2BM00026A (incorporated by reference), Citrate-based Biodegradable Injectable hydrogel Composites for Orthopedic Applications Dipendra Gyawali, a, b, Parvathi Nair, a, b, Harry K. W. Kim, c, and Jian Yang (incorporated by reference).

What is claimed is:

1. A method of re-configuring tissue to affect the external appearance of a human comprising
    assessing a current tissue configuration;
    urging said tissue to a desired tissue configuration;
    designating at least one fixation point associated said desired tissue configuration;
    cutting tissue at each fixation point;
    dissecting said tissue with a dissecting tool and creating a specific volume of space beneath a fat layer of said tissue so as to form a pocket space between 1-50 mm$^3$, beneath said fat layer;
    injecting a volume of adhesive in a range of 0.1 cc to 5 cc through a delivery tool into said pocket space until said pocket space is filled with said adhesive;
    holding said tissue at said fixation point until said adhesive cures sufficiently to thereby hold the tissue at said fixation point without the need for further holding.

2. A method according to claim 1, wherein the pocket space is formed in a supra periosteal space.

3. A method according to claim 1, wherein the pocket space is formed in subcutaneous space.

4. A method according to claim 1, wherein said desired tissue configuration is a brow lift.

5. A method according to claim 1, wherein said desired tissue configuration is a facelift.

6. A method according to claim 1, wherein said desired tissue configuration is a necklift.

7. A method according to claim 1, wherein said creating a specific volume of space comprises inserting a tip of said dissecting tool into said tissue and undermining the tissue below said fat layer.

8. A method according to claim 1, wherein said cutting comprising making an incision less than 2 mm.

9. A method according to claim 1, wherein said creating a specific volume of space comprises forming a pocket space 2 cm in diameter.

10. A method according to claim 1, wherein said dissecting tool and said delivery tool are the same tool.

11. A method of re-configuring tissue to affect the external appearance of a human comprising
    assessing a current tissue configuration;
    urging said tissue to a desired tissue configuration;
    designating at least one fixation point associated said desired tissue configuration;
    cutting tissue at each fixation point by making an incision in a range of 0.5-3 mm;
    dissecting said tissue with a dissecting tool and creating a specific volume of space beneath a fat layer of said tissue so as to form a pocket space beneath said fat layer;
    injecting a volume of adhesive in a range of 0.1 cc to 5 cc through a delivery tool into said pocket space until said pocket space is filled with said adhesive;
    holding said tissue at said fixation point until said adhesive cures sufficiently to thereby hold the tissue at said fixation point without the need for further holding.

12. A method according to claim 11, wherein the pocket space is formed in a supra periosteal space.

13. A method according to claim 11, wherein the pocket space is formed in subcutaneous space.

14. A method according to claim 11, wherein said desired tissue configuration is a brow lift.

15. A method according to claim 11, wherein said desired tissue configuration is a facelift.

16. A method according to claim 11, wherein said desired tissue configuration is a necklift.

17. A method according to claim 11, wherein said creating a specific volume of space comprises inserting a tip of said dissecting tool into said tissue and undermining the tissue below said fat layer.

18. A method according to claim 11, wherein said cutting comprising making an incision less than 2 mm.

19. A method according to claim 11, wherein said creating a specific volume of space comprises forming a pocket space 2 cm in diameter.

20. A method according to claim 11, wherein said dissecting tool and said delivery tool are the same tool.

* * * * *